United States Patent [19]

Kurtz, Jr. et al.

[11] 4,073,930

[45] Feb. 14, 1978

[54] CARBAMOYLOXIMES AND OXIMES AND INSECTICIDAL AND MITICIDAL COMPOSITIONS AND METHODS EMPLOYING THEM

[75] Inventors: Arthur Peter Kurtz, Jr., Charleston; Themistocles D. J. D'Silva, South Charleston, both of W. Va.

[73] Assignee: Union Carbide Corporation, New York, N.Y.

[21] Appl. No.: 691,374

[22] Filed: June 1, 1976

[51] Int. Cl.² .................. A61K 31/385; A61K 31/40; A61K 31/445; A61K 31/535

[52] U.S. Cl. ............................. 424/277; 260/293.68; 260/326.35; 424/267; 424/274; 544/145; 424/248.51

[58] Field of Search .......... 260/327 M, 327 P, 327 T, 260/293.68, 326.35, 247.1 P; 424/248, 267, 274, 277

[56] References Cited

U.S. PATENT DOCUMENTS

| | | | |
|---|---|---|---|
| 3,066,149 | 11/1962 | Slezak | 260/327 |
| 3,193,561 | 7/1965 | Addor | 260/327 |
| 3,365,361 | 1/1968 | Addor | 167/33 |
| 3,467,672 | 9/1969 | Addor | 260/327 |
| 3,661,930 | 5/1972 | Ghosh | 260/327 R |
| 3,678,075 | 7/1972 | Nikles | 260/327 M |
| 3,770,769 | 11/1973 | Schneider | 260/327 M |
| 3,819,649 | 6/1974 | Zumach | 260/327 M |
| 3,832,400 | 8/1974 | Meyer | 260/566 AC |
| 3,875,232 | 4/1975 | Magee | 260/566 |
| 3,928,382 | 12/1975 | Addor | 260/327 M |
| 3,956,500 | 5/1976 | Durden | 424/276 |

OTHER PUBLICATIONS

Smith, Chem. of Open–Chain Org. N–Cpds, vol. II, (Benjamin, N.Y., 1966), pp. 362–363, 465–469.

*Primary Examiner*—Cecilia M. S. Jaisle
*Attorney, Agent, or Firm*—Richard C. Stewart

[57] ABSTRACT

2-Oximino-1,3,5-trithiane compounds are useful intermediates in the preparation of 1,3,5-trithiane carbamoyloxime compounds which exhibit outstanding pesticidal activity.

43 Claims, No Drawings

CARBAMOYLOXIMES AND OXIMES AND INSECTICIDAL AND MITICIDAL COMPOSITIONS AND METHODS EMPLOYING THEM

This invention relates to 1,3,5-trithiane oxime and carbamoyloxime compounds and to their preparation. This invention is also directed to insecticidal and miticidal compositions comprising an acceptable carrier and an insecticidally and miticidally effective amount of a carbamoyloxime compound of this invention and to a method of controlling insects and mites by subjecting them to an insecticidally or miticidally effective amount of a carbamoyloxime compound of this invention.

More particularly this invention relates to compounds of the formula:

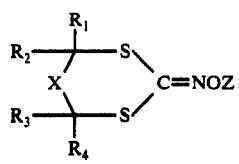

wherein:
X is sulfur, sulfinyl or sulfonyl;
$R_1$, $R_2$, $R_3$ and $R_4$ are individually hydrogen or alkyl;
Z is hydrogen or

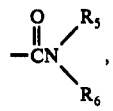

wherein:
$R_5$ is hydrogen, alkyl or cycloalkyl; and
$R_6$ is:
  A. phenyl, either unsubstituted or substituted with one or more fluoro, chloro, bromo, nitro, cyano, trihalomethyl, alkyl or alkoxy substituents; or
  B. When $R_5$ is other than hydrogen, $R_6$ may also be alkylsulfenyl, cycloalkylsulfenyl, alkylthiosulfenyl, cycloalkylthiosulfenyl, naphthylsulfenyl, naphthylthiosulfenyl, trihalomethanesulfenyl, perhaloethanesulfenyl, dialkylaminosulfenyl, piperidylsulfenyl, pyrrolidylsulfenyl, morpholinosulfenyl, alkanoyl, haloalkanoyl or substituted or unsubstituted phenylsulfenyl or phenylthiosulfenyl wherein the permissible substituents are one or more fluoro, chloro, bromo, nitro, cyano, trihalomethyl, alkoxy or alkyl substituents.

In general, the total number of aliphatic carbons included in any one $R_1$, $R_2$, $R_3$, $R_4$, $R_5$ and $R_6$ substituent individually may not exceed six. Preferred because of their higher level of pesticidal activity or because of their usefulness as intermediates in the preparation of carbamoyloxime compounds that exhibit outstanding pesticidal activity are the compounds of this invention in which:
X is sulfur;
$R_1$, $R_2$, $R_3$ and $R_4$ are individually hydrogen or alkyl;
Z is hydrogen or

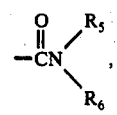

wherein:
$R_5$ is alkyl; and
$R_6$ is alkylsulfenyl, alkylthiosulfenyl, phenylsulfenyl, phenylthiosulfenyl, piperidylsulfenyl, pyrrolidylsulfenyl, morpholinesulfenyl, dialkylaminosulfenyl, trihalomethanesulfenyl or p-tert-butylphenylthiosulfenyl, with the proviso that $R_5$ and $R_6$ individually may not include more than four aliphatic carbons.

The carbamoyloxime compounds of this invention are those of the above formula in which Z is

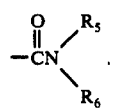

These compounds exhibit outstanding miticidal and insecticidal activities. They are relatively non-toxic to plants and mammals when used in amounts sufficient to kill insects and mites.

The oxime compounds of this invention are those of the above formula in which Z is hydrogen. These compounds are useful as intermediates in the preparation of insecticidally and miticidally active carbamate compounds. For example, 2-oximino-1,3,5-trithiane can be reacted with an appropriately substituted carbamoyl halide such as N-methyl-N-trichloromethanesulfenyl carbamoyl fluoride in the presence of an acid acceptor such as triethylamine to produce 2-[N-trichloromethanesulfenyl-N-methylcarbamoyloximino]-1,3,5-trithiane, the corresponding pesticidally active carbamate ester. The oxime compounds of this invention can also be reacted with other chemical species containing electron deficient reaction sites such as isocyanates and phosgene followed by aminolization with an appropriately substituted amine, to prepare pesticidally active carbamate compounds. These reactions are disclosed in more detail below.

The compounds of this invention can be prepared by a variety of different methods as described below. In these preocedures $R_1$, $R_2$, $R_3$, $R_4$, $R_5$, $R_6$ and X are as described above and Y is chlorine or fluorine, except as noted. One method of preparing the oxime compounds of this invention is by sequentially reacting an appropriately substituted 1,3,5-trithiane compound with an acid acceptor and a nitrite ester followed by nuetralization with acid as illustrated in the following reaction scheme:

METHOD I

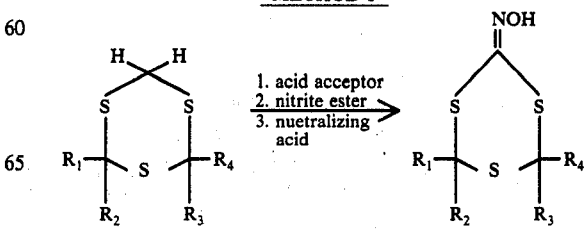

Three preferred methods for preparing the carbamoyloxime compounds of this invention are illustrated by the general reaction schemes set forth below:

METHOD II

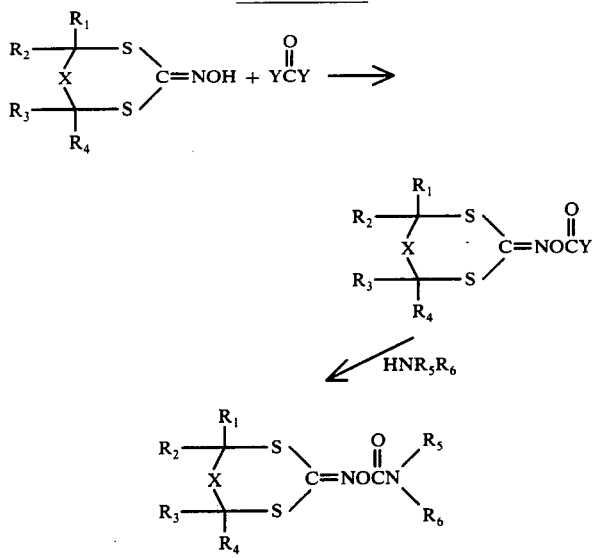

In Method II, $R_5$ is alkyl or cycloalkyl and $R_6$ is substituted or unsubstituted phenyl.

METHOD III

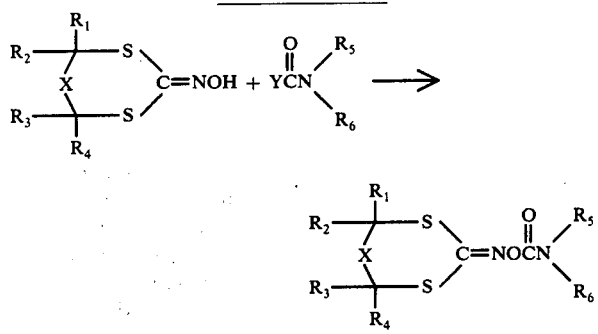

METHOD IV

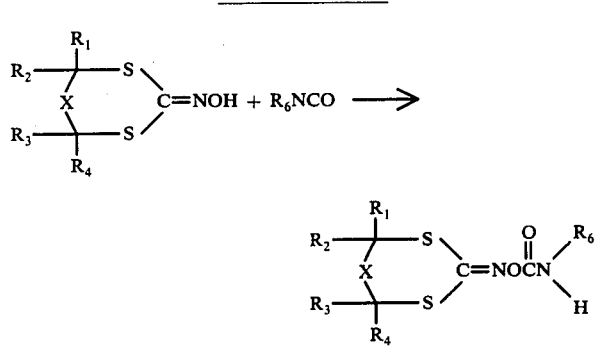

$R_6$ in Method IV is unsubstituted or substituted phenyl.

The reactions illustrated in methods I, II, III and IV can be conducted under similar reaction conditions. Substantially equimolar amounts of the reactants are mixed together in an inert solvent. Any inert solvent such as benzene, toluene, xylene, dioxane, tetrahydrofuran or the like can be used. The reaction illustrated in Method I is preferably conducted in an anhydrous inert solvent.

Reaction temperatures and pressures are not critical. The reaction can be conducted at a temperature of from about −30° C to about 100° C. When an alkali metal alkylide is employed as an acid acceptor in the reaction of Method I, the reaction is preferably conducted at a temperature of from about −60° C to about 0° C. For convenience these reactions are usually conducted at atmospheric or autogenous pressure.

These reactions can be conducted in either a homogeneous phase system or a heterogenous phase system. In the latter case a phase transfer agent such as a crown ether, a quaternary ammonium halide or the like may be used to facilitate the transfer of the reactants across the phase interface.

The reactions illustrated in Methods I, II and III are conducted in the presence of an acid acceptor. The acid acceptor employed can be either an organic base or an inorganic base. Illustrative of organic bases which may be employed as acid acceptor in the conduct of these reactions are tertiary amines, alkali metal alkoxides, alkali metal alkylides or the like. Alkali metal hydroxides such as sodium hydroxide, potassium hydroxide or the like are illustrative of inorganic bases which are useful as acid acceptors. Preferred acid acceptors in the conduct of the reactions of Methods II and III are tertiary amines such as triethylamine, pyridine, 1,4-diazabicyclo[2.2.2] octane or the like. The acid acceptor employed in the reaction illustrated in Method I is preferably an alkali metal alkylide such as butyl lithium or the like. The molar ratio of acid acceptor to either reactant is equimolar or a slight excess of acid acceptor may be used.

The reaction illustrated in Method IV is preferably conducted in the presence of a catalyst. In general, any conventional catalyst of the type commonly employed to promote reactions between isocyanate compounds and compounds which contain an active hydrogen may be used. Preferred catalyst are tertiary amines such as triethylamine, pyridine or the like. Generally, the reaction is conducted in the presence of a quantity of catalyst sufficient to provide a suitable and reasonable reaction rate.

A nitrite ester and a nuetralizing acid are reagents in the reaction shown in Method I. Illustrative of nitrite esters which are useful are alkyl nitrite esters such as isobutylnitrite, ethylnitrite or the like. After the reaction has gone to completion usually in from 0.5 hours to 20 hours, the oxime salt is neutralized by the addition of an acid. Any conventional organic or inorganic acid can be used, as for example, hydrochloric acid and acetic acid.

Carbamoyloxime and oxime compounds of this invention wherein X is sulfinyl or sulfonyl can be prepared by electively oxidising the 5-sulfide linkage of the corresponding 1,3,5-trithiane 2-carbamoyloxime compound or 1,3,5-trithiane 2-oxime compound.

Compounds of this invention in which $R_6$ is alkanoyl or haloalkanoyl can be prepared by reacting the corresponding compound in which $R_6$ is hydrogen with an appropriately substituted alkanoyl halide or anhydride compound.

Isocyanate, carbonyl chloride, carbonylfluoride and amine precursors are well known compounds. Oxime compounds can be prepared as described hereinabove.

Carbamoyl halide precursors used in the preparation of the carbamate compounds of this invention can be prepared by a variety of conventional methods. The choice of method is influenced to a large extent by $R_6$ substituent patterns. For example, carbamoyl fluoride precursors in which $R_6$ is a thiosulfenyl, sulfenyl or an aminosulfenyl substituent can be prepared by reacting hydrogen fluoride with an appropriately substituted isocyanate to form the mono-substituted carbamoyl fluoride which is then reacted in the presence of an acid acceptor with either a thiosulfenyl chloride, a sulfenyl chloride or an aminosulfenyl chloride to produce the corresponding N-thiosulfenylated, N-sulfenylated or N-aminosulfenylated carbamoyl fluoride, respectively. For example, hydrogen fluoride can be reacted with methyl isocyanate dissolved in toluene to produce N-methyl carbamic acid fluoride which, in turn, can be reacted with either 1-piperidinosulfenyl chloride, n-hexylthiosulfenyl chloride or p-tert-butylphenylsulfenyl chloride, in the presence of essentially an equivalent amount of triethylamine, to produce either N-methyl-N-(1-piperidinosulfenyl)carbamoyl fluoride, N-methyl-N-(n-hexylthiosulfenyl)carbamoyl fluoride, or N-methyl-N-(p-tert-butylphenylsulfenyl)carbamoyl fluoride, respectively.

N-sulfenylamino reactants can be conveniently prepared by either reacting the corresponding secondary amine and sulfur dichloride or by the chlorination of the corresponding bis-amine-disulfide as disclosed in British Pat. No. 790,021, German Pat. No. 1,131,222 and U.S. Pat. No. 3,400,125.

The remaining carbamic acid halide precursors in which $R_5$ and/or $R_6$ are bonded to nitrogen through carbon nitrogen bond can be prepared by reacting an appropriately substituted amine with a carbonyl halide such as phosgene in the presence of an acid acceptor.

Heterocyclic precursors used in the preparation of the oxime compounds of this invention can be prepared according to conventional methods. For example, trithiane heterocyclic precursors can be prepared by condensing either the corresponding bis-(mercaptoalkyl)-sulfide with dihalomethane or by condensing an appropriately substituted aldehyde with hydrogen sulfide. The above described procedures are disclosed in more detail in U.S. Pat. No. 2,595,173, German Pat. No. 762,037, T. A. Stanfield and L. B. Reynolds, Jr., J. Amer. Chem. Soc., 74, 2878 (1952), E. Campaign et al. J. Org. Chem. 27, 135 (1962) and references cited therein.

The following specific examples are presented to more particularly illustrate the invention.

EXAMPLE I

Preparation of 2-Oximino-1,3,5-trithiane

To a slurry of 27.6 grams of 1,3,5-trithiane in 500 ml of anhydrous tetrahydrofuran held at $-25°$ C under nitrogen, was added with stirring 130 ml of a 1.6 M solution of butyl lithium in hexane over a period of forty minutes. The cold mixture was stirred for four hours at $-15°$ C. The mixture was then added over a 75 minute period to a solution of 24 grams of ethyl nitrite dissolved in 150 ml of tetrahydrofuran held at $-25°$ C. The reaction mixture was then allowed to warm to ambient temperature and then stirred for 18 hours. The reaction mixture was then cooled to 10° C and neutralized with a solution of 20 ml of concentrated hydrochloric acid dissolved in 80 ml of ethanol. The resulting slurry was concentrated at reduced pressure to 300 ml and poured into a mixture of 300 ml of water and 500 ml of ether. The phases were allowed to equilibrate and then filtered. The filtrate was separated into water and ether phases. The water phase was extracted with 500 ml of ether. The two ether portions were combined and dried over $M_gSO_4$. The ether phase was evaporated under reduced pressure to yield 16 g of a thick oil which solidified on standing. Recrystallization from 200 ml of hot toluene yielded 9.2 grams of 2-oximino-1,3,5-trithiane, mp 105°–107°.

Analysis:
Calc'd for $C_3H_5NOS_3$: C,21.54; H:3.01; N:8.37
Found: C,21.85; H:2.98; N:8.38
NMR (acetone-$d_6$): $\delta 4.27$ (S) $(CH_2)$; $\delta 4.30$ (S), $CH_2$ and $\delta 11.73$ (S), NOH.
IR (KBr): 3.2, 3.4, 6.3, 7.0–7.4 8.6, 9.1 and 10.5$\mu$.

EXAMPLE II

Preparation of 2-[N-Trichloromethanesulfenyl-N-methyl-carbamoyloximino]-1,3,5-trithane A quantity of 2.8 g of N-methyl-N-trichloromethanesulfenylcarbamoyl fluoride, previously prepared by the Method described in West German Pat. No. 1,297,095, 2.0 g of 2-oximino-1,3,5-trithiane and 1.7 ml of triethyl amine were added to 125 ml of tetrahydrofuran. The reagents were allowed to react in a manner similar to that used in Netherlands Pat. No. 7,404,474. Conventional workup and recrystallization from acetone/isopropyl ether yielded 2.9 g of 2-[N-Trichloromethanesulfenyl-N-methylcarbamoyloximino]-1,3,5-trithiane, mp. 118°–119° C.

Calc'd for $C_6H_7Cl_3N_2O_2S_4$: C, 19.28, H, 1.89; N, 7.49
Found: C, 19.43; H, 1.94; H, 7.46
NMR (DMSO-$d_6$); $\delta 3.53$ (S) $CH_3$, $\delta 4.41$ (S) $(CH_2)$ and 4.46 (S) $CH_2$.
IR(KBr): 5.7 (C=O), 6.58, 9.0, 9.7, 10.5, 10.6 12.4, 12.85 and 13.2 – 14.5 $\mu$.

EXAMPLE III

Preparation of 2-[N-(N'-Morpholinosulfenyl)-N-methylcarbamoyloximio]-1,3,5-trithiane A quantity of 10 g of 2-oximino-1,3,5-trithiane and 1.26 g of N-(N'morpholinosulfenyl)-N-methylcarbamyl fluoride, prepared as outlined in United States Patent Application Serial No. 486,631, were caused to be reacted in a manner similar to that in Example II. Conventional workup and recrystallization from benzene/isopropyl ether yielded 1.38 g of 2-[N-(N'-morpholinosulfenyl)-N-methyl-carbamoyloximino]-1,3,5-trithiane, m.p. 149°–151° C.

Calc'd for $C_9H_{15}N_3O_3S_4$: C, 31.65; H, 4.43; N, 12.30
Found: C, 32.24; H, 4.30; N, 12.09
NMR (ppm, CDCl$_3$); $\delta 4.17$ (S) $CH_2$; 4.22 (S) $CH_2$; and 3.43 (S) $(CH_3)$; triplets at 3.32 (4H) and 3.70 (4H).
IR (KBr); 3.35, 3.48, 5.78 (C=O); 7.8, 7.9, 8.5, 9.0, 9.2, 10.6, 11.42, 13.26, 13.5$\mu$.

EXAMPLE IV

Preparation of 2-[N-(t-butylthiosulfenyl)-N-Methylcarbamoyloximino]-1,3,5-trithiane A quantity of 2.0 g of 2-oximino-1,3,5-trithiane and 2.35 g of N-t-butylthiosulfenyl-N-methylcarbamoyl fluoride, prepared as outlined in U.S. Patent Application Ser. No. 486,631 were caused to react in a manner similar to that used in Example III. Conventional workup and recrystallization from acetone/isopropyl ether yielded 1.4 g of 2-[N-(t-butylthiosulfenyl)-N-methylcarbamoyloximino]-1,3,5-trithiane, m.p. 124°–126°.

Calc'd for $C_9H_{16}N_2O_2S_5$: C, 31.37; H, 4.68; N, 8.13
Found: C, 31.18; H, 4.57; N, 8.08
NMR: $(CDCl_3)$: δ4.23 (S) $(CH_2,)$ 4.18 (S) $CH_2$, 3.27 (S) $CH_3$ and 1.41 (S) (t-butyl).
IR(KBr): 3.36, 5.77 (C=O), 6.61, 7.78, 8.60, 9.20, 9.78, 10.6, 11.5, 12.75, 13.5μ.

EXAMPLE V

Preparation of N-Methyl-N(methylthiosulfenyl)carbamoyl Fluoride

To a solution of 7.59 g of hydrogen fluoride in 50 ml of toluene, cooled to −50° C was added dropwise with stirring to 21.62 g of methyl isocyanate. After stirring for 1 hour, 55.0 g of methyl thiosulfenyl chloride in 200 ml of toluene was added followed by dropwise addition of 38.3 g of triethylamine. The reaction temperature during the addition of base was maintained between 0° and 10° C. Stirring was continued for an additional one hour after the addition of base as completed. The precipitated salt was filtered off and the filtrate concentrated under vacuo. Distillation yielded 16.7 g of N-methyl-N(methylthiosulfenyl)carbamoyl fluoride, b.p. 42° C/0.2 Torr.

Calc'd. for $C_3H_6F NOS_2$: C, 23.22; H, 3.89 N, 9.02
Found: C, 23.39; H, 4.18; N, 8.75
IR (Neat): 5.58 (C=O), 7.05, 7.77, 8.4, 8.6, 9.2, 9.35, 10.6, 13.4 and 14.35μ.
NMR $(CDCl_3)$: δ2.69, (Singlet), 3H, $CH_3S$; δ3.28 (doublet), J = 1.0$H_z$, 3H, $CH_3N$.

EXAMPLE VI

Preparation of N-Methyl-N-(4-Morpholinosulfenyl) carbamoyl Fluoride

Anhydrous hydrogen fluoride (3.4 g, 0.17 mole) was added to 200 ml of toluene at −10° C. in a polyethylene reactor equipped with a stainless steel stirrer and thermocouple well, and a polyethylene dry ice condenser. Methyl isocyanate (9.35 g, 0.17 mole) was then added dropwise; the temperature was maintained at −10° C. or less. Then, 26.3 g (0.17 mole) of freshly distilled 4-morpholinosulfenyl chloride was added to the mixture over a 20 minute period, and finally, 17.3 g (0.17 mole) of triethylamine was added at −10° C. After the addition was completed the mixture was stirred and allowed to warm to room temperature for 30 minutes. It was filtered and the filtrate was extracted twice with water and dried with magnesium sulfate. The toluene was removed in vacuo, and the residue was dissolved in boiling hexane, treated with decolorizing charcoal, filtered and chilled. The resulting crystals were collected by suction filtration, and dried in vacuo to give 20 g. of N-Methyl-N-(4-morpholinosulfenyl)carbamoyl fluoride, m.p. 48°–50° C. (60.5 per cent yield.)

Calc'd: $C_6H_{11}F N_2O_2S$: C, 37.10; H, 5.71; N, 14.42
Found: C, 36.44; H, 5.57; N, 14.02

The following compounds are representative of other compounds that are within the scope of this invention which can be prepared according to this invention by selecting appropriate starting materials for use in the procedures described above:

2-(N-Acetyl-N-methylcarbamoyloximino)-1,3,5-trithiane.
2-(N-Chloroacetyl-N-ethylcarbamoyloximino)-1,3,5-trithiane.
4-(N-Phenyl-N-methylcarbamoyloximino)-1,3,5-trithiane-1-oxide.
2-[N-(3-Trifluoromethylphenylsulfenyl)-N-methylcarbamoyl oximino]-1,3,5-trithiane.
2-[N-Hexylsulfenyl-N-methylcarbamoyloximino]1,3,5-trithiane.
2-[N-Trifluoromethanesulfenyl-N-methylcarbamoyloximino]-1,3,5-trithiane.
2-[N-Trichloromethanesulfenyl-N-methylcarbamoyloximino]-1,3,5-trithiane.
2-[N-t-Butylthiosulfenyl-N-methylcarbamoyloximino]-4,6-dipropyl-1,3,5-trithiane.
2-[N-Isopropylthiosulfenyl-N-methylcarbamoyloximino]-4,6-dipropyl-1,3,5-trithiane.
2-[N-tert-Butylthiosulfenyl-N-methylcarbamoyloximino]-4,6-dimethyl-1,3,5-trithiane.
2-[N-(4-Isopropylphenylsulfenyl)-N-methylcarbamoyloximino]1,3,5-trithiane.
2-[N-(4-tert-Butylphenylthiosulfenyl)-N-methylcarbamoyloximino]-1,3,5-trithiane.
2-[N-(Dimethylaminosulfenyl)-N-methylcarbamoyloximino]-4,6-dimethyl-1,3,5-trithiane.
4-[N-(N'-Isopropyl-N'-methylaminosulfenyl)-N-methylcarbamoyloximino]-1,3,5-trithiane-1,1-dioxide.
2-[N-(N'-Piperidinosulfenyl)-N-propylcarbamoyloximino]-1,3,5-trithiane.
2-[N-(N'-Morpholinosulfenyl)-N-methylcarbomoyloximino]-1,3,5-trithiane.
2-[N-(N'-Piperidinosulfenyl)-N-methylcarbamoyloximino]-diethyl-1,3,5-trithiane.
2-[N-Cyclohexylthiosulfenyl-N-methylcarbamoyloximino]-1,3,5-trithiane.
2-[N-(4-Chlorophenylthiosulfenyl)-N-methylcarbamoyl-oximino]-1,3,5-trithiane.
2-[N-(4-Nitrophenylthiosulfenyl)-N-methylcarbamoyloximino]1,3,5-trithiane-5,5-dioxide.
2-[N-(4-tert-Butyl-2-methylphenylsulfenyl)-N-methylcarbamoyloximino]-1,3,5-trithiane.
2-[N-(Phenylsulfenyl)-N-methylcarbamoyloximino]1,3,5-trithiane.
2-[N-(Phenylthiosulfenyl)-N-methylcarbamoyloximino]-1,3,5-trithiane.
2-[N-(Tetrachloroethanesulfenyl-N-methylcarbamoyloximino]-1,3,5-trithiane.
2-Oximino-1,3,5-trithiane.
4-Oximino-1,3,5-trithiane-1,1-dioxide.
2-Oximino-4,6-dimethyl-1,3,5-trithiane.
4-Oximino-1,3,5-trithiane-1-oxide.
4-Oximino-2,6-dipropyl-1,3,5-trithiane.
2-Oximino-4,6-diethyl-1,3,5-trithiane.
2-Oximino-4,6-dihexyl-1,3,5-trithiane.
4-Oximino-2,2-dimethyl-1,3,5-trithiane.
2-Oximino-4,4,6,6-tetrahexyl-1,3,5-trithiane.
2-[N-Napthylthiosulfenyl-N-pentylcarbamoyloximino]1,3,5-trithiane.
2-[N-Hexanoyl-N-3-methylcarbamoyloximino]-1,3,5-trithiane.
2-[N-(2-Chloroethanoyl)-N-methylcarbamoyloximino]-1,3,5-trithiane.
2-[N-Cyclohexyl-N-phenylcarbamoyloximino]-1,3,5-trithiane.
2-[N-Cyclopentylsulfenyl-N-ethylcarbamoyloximino]-1,3,5-trithiane.
2-[N-(4-Trifluoromethylphenylsulfenyl)-N-methylcarbamoyloximino]-1,3,5-trithiane.

2-[N-(4-Cyanophenylthiosulfenyl)-N-pentylcarbamoyloximino]-1,3,5-trithiane.

2-[N-(2-Ethoxyphenylsulfenyl)-N-propylcarbamoyloximino]-1,3,5-trithiane.

4-[N-(2-Bromophenyl)-N-methylcarbamoyloximino]-1,3,5-trithiane-1-oxide.

2-[N-(4-Nitrophenyl)-N-methylcarbamoyloximino]-1,3,5-trithiane.

4-[N-(4-Cyanophenyl)-N-methylcarbamoyloximino]-1,3,5-trithiane-1-oxide.

2-[N-(2,4-Dichlorophenyl)-N-cyclohexylcarbamoyloximino]-1,3,5-trithiane.

4-[N-(2,4-Dimethylphenyl)-N-methylcarbamoyloximino]-1,3,5-trithiane-1,1-dioxide.

2-[N-(2-Trichloromethyl-4-methoxyphenyl)-N-methylcarbamoyloximino]-1,3,5-trithiane.

2-[N-(N'-Pyrrolidylsulfenyl)-N-methylcarbamoyloximino]-1,3,5-trithiane.

2-[N-(3-Ethoxyphenylthio-sulfenyl)-N-methylcarbamoyloximino]-1,3,5-trithiane.

2-[N-(2-Cyano-4-nitrophenylsulfenyl)-N-methylcarbamoyloximino]-4,6-dimethyl-1,3,5-trithiane.

Selected species of the new compounds were evaluated to determine their pesticidal activity against mites and certain insects, including an aphid, a boll weevil, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinabove were obtained by appropriate dilutions of the stock suspension with water. The test procedures were as follows.

Bean Aphid Foliage Spray Test

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialties Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of the leaves of the test plants. Any individual which was capable of locomotion upon prodding was considered living.

The results of these tests are set forth in Table I below. In these tests the pesticidal activity of the compounds against aphid, mite, Southern Armyworm, Mexican Bean Beetle, and house fly was rated as follows:

A = Excellent control
B = Partial control
C = No control

The results of all these tests are set forth in Table I below:

TABLE I

| Compound | APHID | MITE | SOUTHERN ARMY-WORM | MEXICAN BEAN-BEETLE | HOUSE-FLY |
|---|---|---|---|---|---|
| (dithiolane)C=NOC(O)N(CH$_3$)SCCl$_3$ | A | A | A | A | A |
| (dithiolane)C=NOC(O)N(CH$_3$)S—S—C(CH$_3$)$_3$ | A | A | A | A | A |
| (dithiolane)C=NOC(O)N(CH$_3$)S—N(morpholino) | A | C | A | A | A | an absorbent cotton pad. This bait cup was introduced and centered on the blotting paper under the food strainer prior to admitting the anesthetized flies. The caged flies were allowed to feed on the bait for twenty four hours, at a temperature of 80° ±5° F. and the relative humidity of 50±5 percent. Flies which showed no sign of movement on prodding were considering dead.

Mite Foliage Spray Test

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants.

It should be understood that the insect species employed in the above tests are merely representative of a wide variety of posts that can be controlled by the use of the carbamoyloxime compounds of this invention. It should be noted that in addition to their insecticidal and miticidal activity these compounds exhibit an acceptable level of nematocidal activity.

The carbamoyloxime compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about one-fourth to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

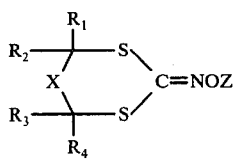

wherein:
X is sulfur, sulfinyl or sulfonyl;
$R_1$, $R_2$, $R_3$ and $R_4$ are individually hydrogen or alkyl;
Z is hydrogen or

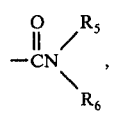

wherein:
$R_5$ is hydrogen, alkyl or cycloalkyl; and $R_6$ is:
A. phenyl either unsubstituted or substituted with one or more fluoro, chloro, bromo, nitro alkyl, cyano, trihalomethyl or alkoxy substituents; or
B. When $R_5$ is other than hydrogen, $R_6$ may also be alkylsulfenyl, cycloalkylsulfenyl, alkylthiosulfenyl, cycloalkylthiosulfenyl, naphthylsulfenyl, naphthylthiosulfenyl, trihalomethanesulfenyl, perhaloethanesulfenyl, dialkylaminosulfenyl, piperidylsulfenyl, pyrrolidylsulfenyl, morpholinosulfenyl, alkanoyl, haloalkanoyl or substituted or unsubstituted phenylsulfenyl or phenylthiosulfenyl wherein the permissible substituents are one or more fluoro, chloro, bromo, nitro, cyano, trihalomethyl, alkoxy or alkyl substituents;

with the proviso that no one $R_1$, $R_2$, $R_3$, $R_4$, $R_5$ and $R_6$ substituent individually includes more than six aliphatic carbons.

2. A compound according to claim 1 wherein Z is hydrogen.

3. A compound according to claim 1 wherein Z is

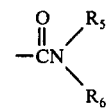

4. A compound according to claim 1 wherein X is sulfur.

5. A compound according to claim 1 wherein X is sulfinyl.

6. A compound according to claim 1 wherein X is sulfonyl.

7. A compound according to claim 1 wherein $R_5$ is alkyl having from 1 to 4 carbons.

8. A compound according to claim 1 wherein $R_5$ is methyl.

9. A compound according to claim 1 wherein $R_6$ is trihalomethanesulfenyl, tetrahaloethanesulfenyl, alkylsulfenyl, alkylthiosulfenyl, phenylsulfenyl, p-tert-butylphenylsulfenyl, dialkylaminosulfenyl, pyrrolidylsulfenyl, piperidylsulfenyl, or morpholinosulfenyl, in which each substituent individually may include from one to six aliphatic carbons.

10. A compound according to claim 1 wherein $R_6$ is trichloromethanesulfenyl, tert-butylthiosulfenyl, morpholinosulfenyl, p-tert-butylphenylsulfenyl, or p-tert-butylphenylthiosulfenyl.

11. A compound according to claim 1 wherein $R_1$, $R_2$, $R_3$ and $R_4$ are individually hydrogen or alkyl having from 1 to 4 carbons.

12. A compound according to claim 1 wherein $R_1$, $R_2$, $R_3$ and $R_4$ are individually hydrogen or methyl.

13. A compound according to claim 1 wherein $R_1$, $R_2$, $R_3$ and $R_4$ are hydrogen.

14. 2-[N-Trichloromethanesulfenyl-N-methylcarbamoyloximino]-1,3,5-trithiane.

15. 2-[N-(tert-Butylthiosulfenyl)-N-methylcarbamoyloximino]-1,3,5-trithiane.

16. 2-Oximino-1,3,5-trithiane.

17. 2-Oximino-1,3,5-trithiane-5,5-dioxide.

18. An insecticidal and miticidal composition comprising an acceptable carrier and an insecticidally or miticidally effective amount of a compound of the formula:

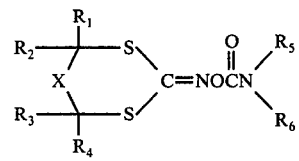

wherein:
X is sulfur, sulfinyl or sulfonyl;
$R_1$, $R_2$, $R_3$ and $R_4$ are individually hydrogen or alkyl;

R₅ is hydrogen, cycloalkyl or alkyl;
R₆ is:
  A. phenyl either unsubstituted or substituted with one or more chloro, bromo, fluoro, nitro, cyano, alkoxy, trihalomethyl or alkyl substituents; or
  B. when R₅ is other than hydrogen R₆ may also be alkylsulfenyl, cycloalkylsulfenyl, cycloalkylthiosulfenyl, alkylthiosulfenyl, naphthylsulfenyl, naphthylthiosulfenyl, trihalomethanesulfenyl, perhaloethanesulfenyl, dialkylaminosulfenyl, iperidylsulfenyl, pyrrolidylsulfenyl, morpholinosulfenyl, alkanoyl haloalkanoyl or substituted or unsubstituted phenylsulfenyl or phenylthiosulfenyl wherein the permissible substituents are one or more chloro, fluoro, bromo, nitro, cyano, alkoxy, trihalomethyl or alkyl in any combination;

with the proviso that any one $R_1$, $R_2$, $R_3$, $R_4$, $R_5$ and $R_6$ substituent individually may not include more than six aliphatic carbons.

19. A composition according to claim 18 wherein X is sulfur.

20. A composition according to claim 18 wherein X is sulfinyl.

21. A composition according to claim 18 wherein X is sulfonyl.

22. A composition according to claim 18 wherein $R_5$ is alkyl having from 1 to 4 carbons.

23. A composition according to claim 18 wherein $R_5$ is methyl.

24. A composition according to claim 18 wherein $R_6$ is trihalomethanesulfenyl, tetrahaloethanesulfenyl, alkylsulfenyl, alkylthiosulfenyl, phenylsulfenyl, p-tert-butylphenylsulfenyl, dialkylaminosulfenyl, pyrrolidylsulfenyl, piperidylsulfenyl, or morpholinosulfenyl, in which each substituent individually may include from one to six aliphatic carbons.

25. A composition according to claim 18 wherein $R_6$ is trichloromethanesulfenyl, tert-butylthiosulfenyl, morpholinosulfenyl, p-tert-butylphenylsulfenyl, or p-tert-butylphenylthiosulfenyl.

26. A composition according to claim 18 wherein $R_1$, $R_2$, $R_3$ and $R_4$ are individually hydrogen or alkyl having from 1 to 4 carbons.

27. A composition according to claim 18 wherein $R_1$, $R_2$, $R_3$ and $R_4$ are individually hydrogen or methyl.

28. A composition according to claim 18 wherein $R_1$, $R_2$, $R_3$ and $R_4$ are hydrogen.

29. A composition according to claim 18 wherein the active toxicant is 2-[N-Trichloromethanesulfenyl-N-methylcarbamoyloximino]-1,3,5-trithiane.

30. A composition according to claim 18 wherein the active toxicant is 2-[N-(tert-butylthiosulfenyl)-N-methylcarbamoyloximino]-1,3,5-trithiane.

31. A method of controlling insects and mites which comprises subjecting them to an insecticidally or miticidally effective amount of a compound of the formula:

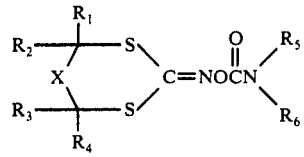

wherein:
X is sulfur, sulfinyl, or sulfonyl;
$R_1$, $R_2$, $R_3$ and $R_4$ are individually hydrogen or alkyl;
R₅ is hydrogen, cycloalkyl or alkyl;
R₆ is:
  A. phenyl either unsubstituted or substituted with one or more chloro, bromo, fluoro, nitro, cyano, alkoxy, trihalomethyl or alkyl substituents; or
  B. when R₅ is other than hydrogen R₆ may also be alkylsulfenyl, cycloalkylsulfenyl, cycloalkylthiosulfenyl, alkylthiosulfenyl, naphthylsulfenyl, naphthylthiosulfenyl, trihalomethanesulfenyl, perhaloethanesulfenyl, dialkylaminosulfenyl, piperidylsulfenyl, pyrrolidylsulfenyl, morpholinosulfenyl, haloalkanoyl alkanoyl or substituted or unsubstituted phenylsulfenyl or phenylthiosulfenyl wherein the permissible substituents are one or more chloro, fluoro, bromo, nitro, cyano, alkoxy trihalomethyl or alkyl in any combination;

with the proviso that any one $R_1$, $R_2$, $R_3$, $R_4$, $R_5$ and $R_6$ substituent may not individually include more than six aliphatic carbons.

32. A method according to claim 31 wherein X is sulfur.

33. A method according to claim 31 wherein X is sulfinyl.

34. A method according to claim 31 wherein X is sulfonyl.

35. A method according to claim 31 wherein $R_5$ is alkyl having from 1 to 4 carbons.

36. A method according to claim 31 wherein $R_5$ is methyl.

37. A method according to claim 31 wherein $R_6$ is trihalomethanesulfenyl, tetrahaloethanesulfenyl, alkylsulfenyl, alkylthiosulfenyl, phenylsulfenyl, p-tert-butylphenylsulfenyl, dialkylaminosulfenyl, pyrrolidylsulfenyl, piperidylsulfenyl, or morpholinosulfenyl, in which each substituent individually may include from one to six aliphatic carbons.

38. A method according to claim 31 wherein $R_6$ is trichloromethanesulfenyl, tert-butylthiosulfenyl, morpholinosulfenyl, p-tert-butylphenylsulfenyl or p-tert-butylphenylthiosulfenyl.

39. A method according to claim 31 wherein $R_1$, $R_2$, $R_3$ and $R_4$ are individually hydrogen or alkyl having from 1 to 4 carbons.

40. A method according to claim 31 wherein $R_1$, $R_2$, $R_3$ and $R_4$ are individually hydrogen or methyl.

41. A method according to claim 31 wherein $R_1$, $R_2$, $R_3$ and $R_4$ are hydrogen.

42. A method according to claim 31 wherein the compound is 2-[N-Trichloromethanesulfenyl-N-methylcarbamoyloximino]-1,3,5-trithiane.

43. A method according to claim 31 wherein the compound is 2-[N-(tert-butylthiosulfenyl)-N-methylcarbamoyloximino]-1,3,5-trithiane.

* * * * *

UNITED STATES PATENT OFFICE
CERTIFICATE OF CORRECTION

Patent No. 4,073,930          Dated February 14, 1978

Inventor(s) Arthur P. Kurtz, Jr.   Themistcoes D.J. D'Silva

It is certified that error appears in the above-identified patent and that said Letters Patent are hereby corrected as shown below:

Column 2, line 49, which reads -- preocedures -- should read "procedures".

Column 10, line 27, which reads -- The dishes -- should read "The closed dishes".

Column 15, line 13, which reads -- iperidylsulfenyl-- should read "piperidylsulfenyl".

Signed and Sealed this

Third Day of October 1978

[SEAL]

Attest:

RUTH C. MASON
*Attesting Officer*

DONALD W. BANNER
*Commissioner of Patents and Trademarks*